United States Patent [19]

Schmidt-Dunker et al.

[11] 4,133,872
[45] Jan. 9, 1979

[54] COMPOSITIONS FOR PREPARATION OF AQUEOUS SOLUTIONS OF SALTS OF LOWER VALENCE $^{99}$TECHNETIUM

[75] Inventors: Manfred Schmidt-Dunker; Wolfgang Greb, both of Düsseldorf, Fed. Rep. of Germany

[73] Assignee: Henkel Kommanditgesellschaft auf Aktien (Henkel KGaA), Düsseldorf, Fed. Rep. of Germany

[21] Appl. No.: 725,772

[22] Filed: Sep. 23, 1976

[30] Foreign Application Priority Data

Sep. 29, 1975 [DE] Fed. Rep. of Germany ....... 2543350

[51] Int. Cl.$^2$ ..................... A61K 29/00; A61K 43/00
[52] U.S. Cl. ............................ 424/1; 260/502.4 R; 260/502.4 P; 260/502.5
[58] Field of Search ................. 260/502.4 R, 502.4 P, 260/502.5, 429 R; 424/1

[56] References Cited

U.S. PATENT DOCUMENTS

| | | | |
|---|---|---|---|
| 3,851,044 | 11/1974 | Adler et al. ............................ | 424/1 |
| 3,965,254 | 6/1976 | Tofe et al. ............................. | 424/1 |
| 3,974,268 | 8/1976 | Subramanian et al. ................ | 424/1 |
| 3,976,762 | 8/1976 | Köhler et al. .......................... | 424/1 |
| 3,983,227 | 9/1976 | Tofe et al. .............................. | 424/1 |
| 3,989,730 | 11/1976 | Subramanian et al. ................ | 424/1 |

*Primary Examiner*—Leland A. Sebastian
*Assistant Examiner*—Christine M. Nucker
*Attorney, Agent, or Firm*—Hammond & Littell

[57] ABSTRACT

Aqueous solutions of $^{99}$technetium salts wherein the $^{99}$technetium is in reduced valencey state, when administered to mammals, permit identification of the skeleton and of calcareous tumors by scintigraphy (radiographic scanning). The solutions are conveniently prepared by mixing one ore more phosphonic acids (or their salts) with one or more reducing salts, and adding the mixture to an aqueous solution of a pharmaceutically acceptable $^{99}$pertechnetate salt. Reduction of the valence of the technetium occurs rapidly, and the resulting solution is adequately stable for use in scintigraphy.

The phosphonic acid and reducing salt components can be premixed. Aqueous solutions of the premix are stable for long periods of time in the absence of free oxygen and the premix is stable to air so long as it is dry.

14 Claims, No Drawings

COMPOSITIONS FOR PREPARATION OF AQUEOUS SOLUTIONS OF SALTS OF LOWER VALENCE $^{99}$ TECHNETIUM

BACKGROUND OF THE INVENTION

The present invention relates to water-soluble compositions or complexes of certain water-soluble phosphonic acids and salts with certain water-soluble polyvalent metal salts, for use in the preparation of stable aqueous solutions containing radioactive $^{99m}$ technetium.

The invention includes the compositions of the phosphonic-polyvalent metal components in tableted dry mix and in aqueous solution forms. The invention also includes aqueous solutions of low valence $^{99m}$ technetium compounds having a content of said phosphonic-polyvalent metal compositions as stabilizer, and methods for the preparation of said solutions.

It has been known for some time that X-ray investigations for recognizing skeletal diseases and tumors, especially in the early stages, are not entirely satisfactory, even when effective treatment is possible. Newer methods have therefore been developed in which the radioactive isotopes fluorine-18 and strontium-85 are used, which are selectively adsorbed in the skeleton and in particular by diseased portions of the skeleton. These radioactive isotopes concentrate even in calcareous tumors. Bone or tissue diseases can then be recognized and their sites identified by radiography. The production of $^{18}F$, however, requires complex apparatus which is usually not present in hospitals and in addition $^{18}F$ has an extremely short half-life (only 110 minutes). The isotope $^{85}Sr$, on the other hand, has a very long half-life (65 days), but this isotope requires very long scanning periods because of its slow rate of decomposition and consequent low radio-emission rate.

Because of these disadvantages, interest has recently been directed to the radio isotope technetium-99$^m$, which has a half-life of 6 hours. Very convenient apparatus is available for its production, by which the isotope is obtained in the form of sodium $^{99m}$ pertechnetate by extraction with isotonic sodium chloride solution. In this form the technetium has a valence of 7.

The pertechnetate-$^{99m}$ ion differs from ions containing $^{18}F$ and from $^{85}Sr^{2+}$ in that in the body the pertechnetate ion is not specially bound in the skeleton or to calcareous tumors. It is therefore not practically useful for the scintigraphic examination of bones and calcareous tumors. In order to use it, therefore, the pertechnetium in the ion must be reduced to a relatively low oxidation state (i.e., to a low valence state) and then stabilized with a suitable complex former in this oxidation state. The valence of the technetium in this reduced state is 4. The complex former must also have a high selectivity for preferred adsorption by the skeleton or by calcareous tumors. Initial successes were achieved with certain polyphosphates whose complexes, however, have only moderate stability with low oxidation state technetium. A suitable complex was produced by mixing $^{99m}$ pertechnetate solution with an aqueous solution of ditin (II) ethane-1-hydroxy-1,1-diphosphonate (described in J. Nucl. Med. 13, 947 and 14, 73). The stability of this ditin (II) ethane-1-hydroxy-1,1-diphosphonate solution was restricted, however, with an excess of ethane-1-hydroxy-1,1-diphosphonate, especially since the tin (II) ion has a tendency to hydrolyze. A composition for the preparation of a material for the scintigraphic scanning of bones on this basis is described in German Patent Specification No. 2,424,496.

It has now been found that certain carboxy phosphonic acids and their salts are very desirable complexing agents because of the high stability of their complexes with ions containing low oxidation state technetium ions and because of the high selectivity with which the $^{99m}$ Tc deposits itself in the bone tissue or in calcareous tumors.

OBJECTS OF THE INVENTION

The object of producing a soluble-stable composition which on addition to aqueous pertechnetate salt solutions provides a stable, effective and selective form of $^{99}$ technetium suitable for the radiography of bones and calcareous tumors, is attained by preparations which contain a mixture of:

(A) at least one water-soluble carboxyphosphonic compound of the theoretical formula:

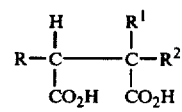

wherein R represents H or $C_{1-3}$ alkyl, and $R^1$ represents $-PO_3H_2$,

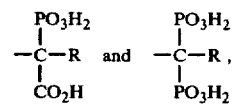

and wherein $R^2$ represents H, $C_{1-3}$ alkyl,

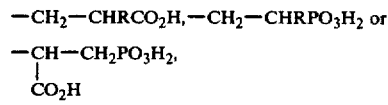

II pharmaceutically useful water-soluble salts of the above compounds, and (B) a pharmaceutically acceptable water-soluble tin (II), iron (II), or chromium (II) salt in less than stoichiometric quantities, based on component (A).

DESCRIPTION OF THE INVENTION

More in detail, we have found that a stable aqueous solution of a physiologically acceptable water-soluble salt of $^{99}$technetium which is preferentially absorbed by bone and by calcareous tumors, is formed when to an aqueous solution of a $^{99}$pertechnetate salt is added a sufficient amount of a composition of a water-soluble phosphonic compound and a water-soluble reducing salt to reduce the technetium in said pertechnetate salt to a lower valence. The reduction in valence occurs rapidly, and the resulting solution, containing 1 to 20 mCi per ml of combined technetium is suitable for intravenous administration for the above purpose. The valence of the reduced technetium is 4.

According to the present invention a suitable amount of $^{99}$technetium compound which is administered for radiographic purposes, is in the range of 0.05 to 0.3 mCi per kilogram of body weight.

It is possible, with these components, to produce in simple fashion highly stable compositions which are suitable for distribution and storage in solid form as tablets or in the form of solutions in an ampoule. After being added to an aqueous solution of a pertechnetate salt, the resulting solution is a very effective agent for diagnosing bone tumors, local disorders in bone metabolism and calcareous tissue tumors by the radiation scanning method.

The above phosphonic compounds can be used in free acid form. However, they can also be used for pharmaceutical purposes in the form of their pharmacologically harmless salts salts such as their sodium, potassium, magnesium, zinc, and ammonium salts, as well as their substituted ammonium salts such as mono-, di- or trialkanolammonium salts. Moreover, the phosphonic acids can be used in the form of their partial salts (where only a portion of the acid protons is substituted by other cations) and in the form of their whole salts. The partial salts, which react substantially neutrally in aqueous solution (providing a pH in the range of 5–9 at 1% concentration) are preferred. Mixtures of the above-mentioned salts may also be used.

Suitable phosphonoalkanepolycarboxylic acids are listed in the Table shown below. Instead of the acids mentioned therein the water-soluble salts of these acids with physiologically harmless cations such as those named above can also be used.

Phosphono-ethane-1,2-dicarboxylic acid
1-Phosphono-propane-1,2-dicarboxylic acid
1-Phosphono-pentane-1,2-dicarboxylic acid
2-Phosphono-propane-2,3-dicarboxylic acid
2-Phosphono-pentane-1,2-dicarboxylic acid
2-Phosphono-butane-2,3-dicarboxylic acid
2-Phosphono-pentane-2,3-dicarboxylic acid
4-Phosphono-octane-4,5-dicarboxylic acid
2-Phosphono-butane-1,2,4-tricarboxylic acid
2-Phosphono-pentane-1,2,4-tricarboxylic acid
2-Phosphono-hexane-1,2,4-tricarboxylic acid
2-Phosphono-heptane-1,2,4-tricarboxylic acid
3-Phosphono-pentane-2,3,5-tricarboxylic acid
3-Phosphono-heptane-1,3,4-tricarboxylic acid
3-Phosphono-hexane-2,3,5-tricarboxylic acid
4-Phosphono-octane-3,4,6-tricarboxylic acid
5-Phosphono-nonane-4,5,7-tricarboxylic acid
3-Phosphono-octane-2,3,5-tricarboxylic acid
1,3-Diphosphono-butane-3,4-dicarboxylic acid
2,4-Diphosphono-pentane-4,5-dicarboxylic acid
3,5-Diphosphono-hexane-5,6-dicarboxylic acid
2,4-Diphosphono-heptane-1,2-dicarboxylic acid
1,3-Diphosphono-pentane-3,4-dicarboxylic acid
1,3-Diphosphono-hexane-3,4-dicarboxylic acid
2,4-Diphosphono-hexane-4,5-dicarboxylic acid
3,5-Diphosphono-octane-5,6-dicarboxylic acid
3,5-Diphosphono-nonane-5,6-dicarboxylic acid
3,5-Diphosphono-octane-2,3-dicarboxylic acid
1,3-Diphosphono-butane-2,3,4-tricarboxylic acid
1,3-Diphosphono-pentane-2,3,4-tricarboxylic acid
1,3-Diphosphono-heptane-2,3,4-tricarboxylic acid
1-Phosphono-propane-1,2,3-tricarboxylic acid
2-Phosphono-butane-2,3,4-tricarboxylic acid
3-Phosphono-pentane-1,2,3-tricarboxylic acid
3-Phosphono-hexane-1,2,3-tricarboxylic acid
3-Phosphono-heptane-2,3,4-tricarboxylic acid
2-Phosphono-hexane-2,3,4-tricarboxylic acid
4-Phosphono-nonane-4,5,6-tricarboxylic acid
2-Phosphono-pentane-2,3,4-tricarboxylic acid
3-Phosphono-heptane-3,4,5-tricarboxylic acid
1-Phosphono-2-methyl-propane-1,2,3-tricarboxylic acid
2-Phosphono-3-ethyl-butane-2,3,4-tricarboxylic acid
3-Phosphono-4-methyl-pentane-3,4,5-tricarboxylic acid
4-Phosphono-5-propyl-hexane-4,5,6-tricarboxylic acid
2-Phosphono-3-methyl-hexane-2,3,4-tricarboxylic acid
4-Phosphono-5-methyl-nonane-4,5,6-tricarboxylic acid
1-Phosphono-2-methyl-pentane-1,2,3,-tricarboxylic acid
2-Phosphono-3-methyl-pentane-2,3,4-tricarboxylic acid
3-Phosphono-4-ethyl-heptane-3,4,5-tricarboxylic acid
1,1-Diphosphono-propane-2,3-dicarboxylic acid
2,2-Diphosphono-butane-3,4-dicarboxylic acid
3,3-Diphosphono-pentane-4,5-dicarboxylic acid
3,3-Diphosphono-hexane-1,2-dicarboxylic acid
2,2-Diphosphono-pentane-3,4-dicarboxylic acid
4,4-Diphosphono-heptane-2,3-dicarboxylic acid
1,1-Diphosphono-pentane-2,3-dicarboxylic acid
3,3-Diphosphono-heptane-4,5-dicarboxylic acid
1,1-Diphosphono-2-methyl-propane-2,3-dicarboxylic acid
2,2-Diphosphono-3-methyl-butane-3,4-dicarboxylic acid
2,2-Diphosphono-3-methyl-pentane-3,4-dicarboxylic acid
3,3-Diphosphono-4-ethyl-heptane-4,5-dicarboxylic acid
2,2-Diphosphono-3-propyl-heptane-3,4-dicarboxylic acid
1-Phosphono-butane-2,3,4-tricarboxylic acid
1-Phosphono-pentane-2,3,4-tricarboxylic acid
1-Phosphono-3-methyl-pentane-2,3,4-tricarboxylic acid
1-Phosphono-3-methyl-heptane-2,3,4-tricarboxylic acid
1-Phosphono-3-propyl-hexane-2,3,4-tricarboxylic acid
1-Phosphono-3-methyl-butane-2,3,4-tricarboxylic acid
1-Phosphono-3-propyl-butane-2,3,4-tricarboxylic acid Particularly good results in respect of the stabilization of $^{99m}$Tc ions in the complex, the avoidance of formation of colloidal particles, and the selectivity of the deposition of $^{99m}$Tc in the skeleton and in calcareous tumors are obtained with the partial sodium salts of the following preferred carboxyphosphonic acids:

1. Phosphono-ethane-1,2-dicarboxylic acid, 2:1 mixture of disodium:trisodium salts,
2. 1-Phosphono-propane-1,2-dicarboxylic acid, 2:1 mixture of disodium:trisodium salts,
3. 2-Phosphono-butane-1,2,4-tricarboxylic acid, trisodium salt.

These preferred carboxyphosphonic acid partial salts provide excellent absorption through the skeleton and very low absorption in the soft tissues except in calcareous tumors. they are predominantly suitable for identifying bone metastases of masto- or prostato- carcinomae.

The phosphonoalkanepolycarboxylic acids used can be produced according to known methods.

1-Phosphonoethane-1,2-dicarboxylic acid can be produced by reacting maleic acid ester with diethylphosphite in the presence of sodium alcoholate and by subsequent saponification of the ester. 2-Phosphonopropane-2,3-dicarboxylic acid can be obtained similarly, but another reaction with methyl chloride is effected before saponification.

1-Phosphonopropane-1,2,3-tricarboxylic acid can be produced by reacting maleic acid ester with phosphonoacetic acid ester in the present of an alcoholate and by subsequent saponification of the ester thus obtained. 1-Phosphonobutane-2,3,4-tricarboxylic acid can be prepared by reacting dimethylphosphite with 1- butene-2,3,4-tricarboxylic acid ester in the presence of sodium alcoholate and by subsequently saponifying the resultant ester to form the desired acid.

By reacting methanediphosphonic acid alkylester with maleic acid alkylester in the presence of sodium alcoholate, an ester is obtained which is converted to 1,1-diphosphono-propane-2,3-dicarboxylic acid by acid hydrolysis.

2-Phosphonobutane-2,3,4-tricarboxylic acid can be prepared by reacting α-diethylphosphonopropionic acid methyl ester with maleic acid diethylester in the presence of an alcoholate and by subsequently saponifying the ester obtained. 2,2-Diphosphonobutane-3,4-dicarboxylic acid can be prepared by reacting maleic acid ester with ethane-1,1-diphosphonic acid ester in the presence of sodium alcoholate followed by acid saponification of the product.

The other phosphonoalkanepolycarboxylic acids are obtained by analogous methods, citraconic acid ester being preferably used instead of the maleic acid ester.

The water-soluble salts referred to above can be produced by complete or partial neutralization of the acids with inorganic bases such as NaOH, KOH and $NH_4OH$, or with organic bases such as alkanolamines, and also with alkali metal carbonates.

The salts of tin (II), iron (II) and chromium (II) with pharmaceutically acceptable anions are added as the reducing agent. Chlorides and sulfates are preferred as anions because of their universally acknowledged safety. Anhydrous tin (II) chloride is preferred because of its high reducing power and also because of the absence of water of crystallization.

This addition serves to reduce the valence of the technetium in the $^{99m}$ pertechnetate ion which is produced by commercial $^{99m}$ pertechnetate generators. The resulting low-oxidation state $^{99m}$ Tc ion can then be complexed by one of the carboxy phosphonate complex formers mentioned and introduced into the organism for absorption by the skeleton or by calcareous tumors in the organism.

Aqueous solutions of the above-mentioned phosphonic acids and tin (II), iron (II) or chromium (II) salts have the undesirable property of oxidizing or hydrolyzing over a relatively long periods of time in contact with air. This behavior can be overcome by sealing the solutions under nitrogen in ampoules, by preparing lyophilizates sealed under nitrogen or under vacuum (so that the mixture contains no free oxygen) or by preparing the composition of the invention in the form of an anhydrous tablet or dragee, so that the composition contains no water. The compositions of the invention may thus be treated and preserved in stable hydrous and anhydrous forms and are not added to the $^{99m}$ pertechnetate solution until the solution is to be used. An excellent agent for bone and tumor radiography is thereby obtained which supplies superior scintillation images with minimal absorption of metal ions by structures in the body.

The required $^{99m}$Tc activity is extremely low with substantially 10 to 15 millicuries (mCi), and the quantity of tin (II) required for its reduction to lower valent state is also extremely small. The amount of reducing agent which is added is at least sufficient to reduce substantially all of the technetium in the pertechnetate ions to a lower valent state. The preferred quantity of tin or other reducing agent, however, is above the quantity stoichiometrically required for the complete reduction of the technetium content of $^{99m}$ pertechnetate ion. Together with the again substantially larger amount of the phosphonate a $^{99m}$Tc-Sn-phosphonate complex (the exact structure of which is not known) is formed which is stabilized by excess phosphonate.

Preferably the compositions of the invention contain the reducing agent in amounts of 1% to 5% based on the weight of the phosphonic components present. It is added at least in sufficient amount to reduce substantially all the technetium present in the pertechnetate salt to lower valence state, and preferably is added in excess thereover.

It is advantageous for pharmaceutically-compatible fillers, such as glucose or sodium chloride, to be present as agents facilitating the handling and measuring of small quantities of the reducing complex-forming composition. Sodium chloride is preferred for this purpose since it helps to maintain the isotonia even when the pertechnetate solution is diluted with sterile water, as is necessary occasionally.

The active components of the composition are mixed until homogeneous and the mixture in any particulate form is placed in standard glass ampoules, or the mixture is compressed to form tablets when it contains glucose, sodium chloride etc. filler. However, it is preferable to produce a solution of the components which is put into standard ampoules in unit dose amount under nitrogen and lyophilized. The lyophilizate is stable under nitrogen or vacuum, that is, in the absence of free oxygen. An aqueous isotonic solution of the components can also be preserved by excluding free oxygen, e.g., by maintaining the solution under nitrogen. The solution thus contains substantially no dissolved free oxygen.

The present invention will be further described, by means of the following Examples. These Examples illustrate preferred embodiments of the invention and are not to be construed in limitation thereof.

(A) COMPOSITIONS

EXAMPLE 1

Into a standard glass ampoule (10–20 ml.) is poured an aqueous sterile solution containing a 8 mg. of a 2:1 mixture of disodium and trisodium phosphonoethane-1,2-dicarboxylates, together with 2 ml. of water and 0.15 mg. of $SnCl_2$. The solution is lyophilized and the ampoule is sealed under vacuum. For the purpose of use, the substance mixture is dissolved in sterile isotonic $^{99m}$ pertechnetate solution and the resulting solution is injected intravenously into a mammal.

EXAMPLE 2

Into a graduated 10 ml. standard ampoule are poured 8 mg. of an 2:1 mixture of disodium and trisodium 1-phosphono-propane-1,2-dicarboxylates and 0.10 mg. of chromium (II) chloride dissolved in 5 ml. of sterile aqueous solution and lyophilized.

EXAMPLE 3

Into a graduated 20 ml. standard ampoule are poured 8 mg. of trisodium 2-phosphono-butane-1,2,4-tricarboxylate and 0.15 mg. of iron (II) sulfate dissolved in 5 ml. of sterile isotonic sodium chloride solution and processed according to Example 1.

EXAMPLE 4

Into a graduated 5 ml. standard ampoule are poured 8 mg. of trisodium 2-phosphono-butane-1,2,4-tricarboxylate and 0.15 mg. of tin (II) chloride dissolved in 5 ml. of sterile aqueous solution and lyophilized.

EXAMPLE 5

8 mg. of a 2:1 mixture of disodium and trisodium 1-phosphono-propane-1,2-dicarboxylates, 0.2 mg. of tin (II) chloride, 45 mg. of sodium chloride, and 26.8 mg. of glucose are compressed to form 80 mg. of mini-tablets. The tablets dissolved quickly in 5 ml. of sterile water and produce an isotonic solution.

EXAMPLE 6

4 mg. of a 2:1 mixture of disodium and trisodium 1-phosphono-propane-1,2-dicarboxylates, 4 mg. of trisodium-2-phosphono-butane-1,2,4-tricarboxylate, 0.2 mg. of iron (II) sulfate, 45 mg. of sodium chloride, and 26.8 mg. of glucose are compressed to form 80 mg. of mini-tablets. The tablets dissolve quickly in 5 ml. of sterile water and produce an isotonic solution.

EXAMPLE 7

Into a 5 ml. standard ampoule are put 8 mg. of a 2:1 mixture of disodium and trisodium phosphono-ethane-1,2-dicarboxylates, 0.07 mg. of tin (II) chloride, and 0.08 mg. of iron (II) sulfate, dissolved in 5 ml. of sterile isotonic sodium chloride solution.

EXAMPLE 8

The procedure of Example 1 is repeated except that the flask is flushed with dry nitrogen before sealing. Results are the same.

(B) From each of these compositions, after the addition of substantially 5 ml. of sodium $^{99m}$ pertechnetate solution with an activity of substantially 50 mCi/ml. and after careful shaking, an agent is obtained in dissolved form which can be dispensed to warm-blooded animals (i.e., to mammals) by intravenous injection. In the case of adult humans weighing about 70 kg., about 1 ml. of the solution is used for skeletal scintillography, the solution being injected slowly. In the case of young mammals, correspondingly smaller quantities based on body weight may be used where necessary. Larger amounts are used for the scintillography of calcareous soft tissue, e.g. calcareous tumors or in cases of advanced calcification atherosclerosis. The solutions are injected preferably 1-2 hours after preparation.

(C) Solutions produced from the mixture according to Example 3 provided excellent results in skeletal scintillography. They proved particularly successful when searching for bone metastases in mammals having mastocarcinoma or prostatocarinoma and they provide an ideal supplement to X-ray diagnostics.

Distribution studies in rats, which are a good model for the human being in these investigations, with activities of 0.01 to 1.0 mCi on $^{99m}$Tc, showed that in the case of the preferred compositions typically about 60% to 70% of the dose passes into the skeleton. After three hours 5% of the activity can still be found in the blood, the remainder being excreted with the urine. This distribution should be considered excellent. The optimum time for the scintillographical scanning is about 3 hours after injection. In the scintillography of calcareous soft tissue, such as tumors, muscular tissue or advanced calcification atherosclerosis other times are optimum after injection. The optional time depends upon the regional blood clearance of the tissue being examined.

We claim:

1. A composition for use in the preparation of aqueous solutions containing $^{99m}$ technetium for use in the detection by scintigraphy of bones and calcareous tumors, comprising:

(A) one or more water-soluble carboxyphosphonic compounds having three carboxylic acid groups selected from the group consisting of compounds of the formula:

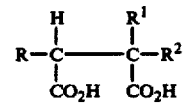

wherein R represents a substituent selected from the group consisting of H and $C_{1-3}$ alkyl;

$R^1$ represents a substituent selected from the group consisting of $-PO_3H_2$, and

$R^2$ represents a substituent selected from the group consisting of

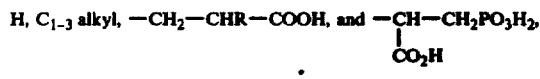

with the proviso that when $R^1$ is $-PO_3H_2$, $R^2$ is other than H or $C_{1-3}$ alkyl; and the pharmaceutically-acceptable water-soluble salts of the above acids; and (B) a pharmaceutically acceptable water-soluble salt selected from the group consisting of tin (II), iron (II) or chromium (II) salts in less than stoichiometric quantities based on component (A).

2. A composition according to claim 1 wherein the weight of component (B) is 1% to 5% of the weight of component (A).

3. A composition according to claim 1 wherein the phosphonic compound is a partial salt.

4. A composition according to claim 1 wherein the phosphonic component comprises a material selected from the group consisting of 2-phosphono-butane-1,2,4-tricarboxylic acid and its trisodium salt.

5. A compound according to claim 1 wherein component (B) is tin (II) chloride.

6. A composition according to claim 1 in dry mix tableted form.

7. A composition according to claim 1 in sterile aqueous solution form.

8. A sterile aqueous solution of a composition according to claim 1 and a $^{99m}$ technetate salt, substantially all the technetium content of said technetate having a valence less than 7.

9. A method of preparing a stable solution of a water-soluble salt of $^{99m}$ technetium which is preferentially absorbed by bone and by calcareous tumors which comprises adding to an aqueous solution of a $^{99m}$ pertechnetate salt a sufficient amount of a composition according to claim 1 to reduce the technetium in said pertechnetate salt to a lower valency.

10. A method according to claim 9 wherein said composition is added to said pertechnetate solution in dry tableted form.

11. A composition for use in the preparation of aqueous solutions containing $^{99m}$ technetium for use in the detection by scintigraphy of bones and calcareous tumors, comprising
(A) 2-phosphono-butane-1,2,4-tricarboxylic acid, and its pharmaceutically-acceptable water-soluble salts; and
(B) a pharmaceutically acceptable water-soluble salt selected from the group consisting of tin (II), iron (II) or chromium (II) salts in less than stoichiometric quantities based on component (A).

12. A composition according to claim 11 wherein the weight of component (B) is 1% to 5% of the weight of component (A).

13. A method of preparing a composition in unit dosage form for the detection by scintigraphy of bones and calcareous tumors by means of $^{99m}$ technetium consisting essentially of
(a) introducing into an ampoule under nitrogen or vacuum an aqueous solution of
(A) one or more water-soluble carboxyphosphonic compounds having three carboxylic acid groups selected from the group consisting of compounds of the formula

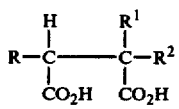

wherein R represents a substituent selected from the group consisting of H and $C_{1-3}$ alkyl;
$R^1$ represents a substituent selected from the group consisting of —$PO_3H_2$, and

$R^2$ represents a substituent selected from the group consisting of H, $C_{1-3}$ alkyl, —$CH_2$—CHR—COOH, and

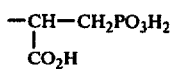

with the proviso that when $R^1$ is —$PO_3H_2$, $R^2$ is other than H or $C_{1-3}$ alkyl; and the pharmaceutically-acceptable water-soluble salts of the above acids; and
(B) a pharmaceutically acceptable water-soluble salt selected from the group consisting of tin (II), iron (II), or chromium (II) salts in less than stoichiometric quantities based on component (A), and (b) thereafter lyophilizing and sealing said aqueous solution in said ampoule under nitrogen or vacuum.

14. A method of preparing a composition in unit dosage form for the detection by scintigraphy of bones and calcareous tumors by means of $^{99m}$ technetium consisting essentially of
(a) introducing into an ampoule under nitrogen or vacuum an aqueous isotonic solution of
(A) one or more water-soluble carboxyphosphonic compounds having three carboxylic acid groups selected from the group consisting of compounds of the formula

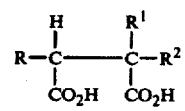

wherein R represents a substituent selected from the group consisting of H and $C_{1-3}$ alkyl;
$R^1$ represents a substituent selected from the group consisting of —$PO_3H_2$, and

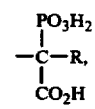

$R^2$ represents a substituent selected from the group consisting of H, $C_{1-3}$ alkyl, —$CH_2$—CHR—COOH, and

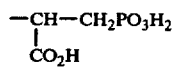

with the proviso that when $R^1$ is —$PO_3H_2$, $R^2$ is other than H or $C_{1-3}$ alkyl; and the pharmaceutically-acceptable water-soluble salts of the above acids; and
(B) a pharmaceutically acceptable water-soluble salt selected from the group consisting of tin (II), iron (II), or chromium (II) salts in less than stoichiometric quantities based on component (A), and
(b) thereafter sealing said aqueous isotonic solution in said ampoule under nitrogen or vacuum.

* * * * *